United States Patent [19]

Kogure

[11] Patent Number: 4,961,927

[45] Date of Patent: Oct. 9, 1990

[54] CLEAR SOLUTION CONTAINING LYSOZYME HYDROCHLORIDE AND DIPOTASSIUM GLYCYRRHIZINATE

[75] Inventor: Yoshio Kogure, Honjou, Japan

[73] Assignee: Eisai Co., Ltd., Tokyo, Japan

[21] Appl. No.: 125,536

[22] Filed: Nov. 25, 1987

[30] Foreign Application Priority Data

Dec. 19, 1986 [JP] Japan .................. 61-303163

[51] Int. Cl.$^5$ .............. A61K 37/54; A61K 31/70; C12N 9/36
[52] U.S. Cl. .................. 424/94.3; 424/94.61; 514/33; 514/887; 514/970; 435/206
[58] Field of Search ............ 424/94.3, 94.61; 435/206; 514/887, 970, 569, 33

[56] References Cited

U.S. PATENT DOCUMENTS 4,469,673 9/1984 Lioka et al. ............... 424/94.61
4,548,950 10/1985 Baxendale et al. .......... 514/887

FOREIGN PATENT DOCUMENTS 2037000 2/1971 France.
49310 3/1983 Japan ................... 514/33
843135 8/1960 United Kingdom.
2122893 1/1984 United Kingdom.

OTHER PUBLICATIONS

Pluripharm, cited in Chem. Abstracts, vol. 75:101266V (1971).
Lion Corp., cited in Chem. Abstracts, vol. 97:133587w (1982).

Primary Examiner—Jacqueline Stone
Attorney, Agent, or Firm—Flynn, Thiel, Boutell & Tanis

[57] ABSTRACT

An aqueous solution comprises lysozyme hydrochloride, dipotassium glycyrrhizinate, at least one selected from the group consisting of sodium chloride, potassium chloride, calcium chloride, magnesium chloride, sodium phosphate, potassium phosphate, sodium citrate, potassium citrate, sodium carbonate and potassium carbonate and water, has a pH of 5 to 9 and is useful for eye drops.

8 Claims, No Drawings

CLEAR SOLUTION CONTAINING LYSOZYME HYDROCHLORIDE AND DIPOTASSIUM GLYCYRRHIZINATE

The present invention relates to a solution containing lysozyme hydrochloride and dipotassium glycyrrhizinate. In particular, the present invention relates to a solution useful in the fields of medicines and cosmetics.

Lysozyme hydrochloride, being an enzyme capable of decomposing mucopolysaccharides contained in various mucuses secreted from tissues, decomposes cell walls of bacteria to show its bacteriolytic effects in an infected patient. When tissue of a patient is inflamed, a membranous mucus produced by the inflammation is decomposed to facilitate the excretion thereof and to exhibit an antiphlogistic effect. Thus, lysozyme hydrochloride is frequently and effectively used in a medical treatment when a mucous membrane of the eyes, nose, throat or ears is inflamed by an infection. Lysozyme hydrochloride is contained in not only preparations to be administered perorally but also those to be directly applied to an affected part in the form of an aqueous solution. A preferred example of the formulations is eye drops which have already been put on the market as a drug for treating chronic conjunctivitis.

Dipotassium glycyrrhizinate has an antiallergic effect and it is useful as a so-called non-steroidal antiinflammatory agent. Its antiinflammatory effect is remarkable particularly on an allergic inflammation of a mucous membrane. Therefore, medicines containing dipotassium glycyrrhizinate have already been put on the market as eye drops to be directly applied in the treatment of, for example, allergic conjunctivitis and allergic blepharitis.

As described above, lysozyme hydrochloride and dipotassium glycyrrhizinate have been used independently from each other as treatments for inflammations of mucous membranes. It is expected, however, that the therapeutic effects are further improved when a combination of them can be used. Namely, it is desired to provide a solution of a mixture of lysozyme hydrochloride and dipotassium glycyrrhizinate to be directly applied to a mucous membrane of eyes, nose, throat or ears.

Such a formulation must satisfy the following two requirements:

(1) the pH of the formulation is adjusted to be in the physiological pH range, i.e. pH 5 to 9, so as to reduce the irritation of the inflammatory mucous membrane of eyes, nose, throat, ears or the like, and (2) the product must be in the form of a clear aqueous solution. In other words, the solution must be filtered to remove bacteria, since the mucous membranes are liable to be infected with bacteria. For this purpose, lysozyme hydrochloride and dipotassium glycyrrhizinate must be dissolved to form a clear solution.

Under these circumstances, the inventor made intensive investigations of the preparation of an aqueous solution containing lysozyme hydrochloride and dipotassium glycyrrhizinate which satisfies both of the above-mentioned requirements. However, the combination of lysozyme hydrochloride with dipotassium glycyrrhizinate immediately formed a precipitate in water to form a milky liquid and thus the preparation of the clear solution was impossible.

SUMMARY OF THE INVENTION

After intensive investigations made for the purpose of solving the above-mentioned problems, the inventors have found that the problems can be solved by adjusting the pH of the solution to 5 to 9 with at least one of sodium chloride, potassium chloride, calcium chloride, magnesium chloride, sodium or potassium phosphate, sodium or potassium citrate and sodium or potassium carbonate. The present invention has been completed on the basis of this finding.

Thus the present invention provides a solution containing lysozyme hydrochloride and dipotassium glycyrrhizinate characterized by having a pH adjusted to 5 to 9 with at least one of sodium chloride, potassium chloride, calcium chloride, magnesium chloride, sodium or potassium phosphate, sodium or potassium citrate and sodium or potassium carbonate.

An aqueous solution of the invention comprises lysozyme hydrochloride, dipotassium glycyrrhizinate, at least one material selected from the group consisting of sodium chloride, potassium chloride, calcium chloride, magnesium chloride, sodium phosphate, potassium phosphate, sodium citrate, potassium citrate, sodium carbonate and potassium carbonate and water and has a pH of 5 to 9.

Now the present invention will be described in detail.

Lysozyme hydrochloride and dipotassium glycyrrhizinate used in the present invention may be those available on the market. In the solution to be directly applied to the affected part, the amounts of lysozyme hydrochloride and dipotassium glycyrrhizinate are usually below 0.5 wt. % and below 0.3 wt. %, respectively. When they are contained in eye drops as a non-prescription drug, the amounts of them are 0.1 to 0.5 wt. % and 0.05 to 0.25 wt. %, respectively, according to the guiding standard of the Ministry of Health and Welfare. Though these concentration ranges are particularly preferred also in the present invention, the concentrations are not limited to them.

The pH of the solution of the present invention is limited to 5 to 9, preferably 6.5 to 8.0. For example, the pH of the eye drops is 7.0 to 7.5 in accordance with the pH of tears. This is a physiological condition necessitated for relieving the irritation of a mucous membrane when the solution is directly applied to the mucous membrane. Particularly when the mucous membrane to which the solution is to be applied is inflamed, its pH must be adjusted to be in the above-mentioned range, since the sensitivity of the membrane is increased by the inflammation.

The solution of the present invention contains at least one of sodium chloride, potassium chloride, calcium chloride, magnesium chloride, sodium or potassium phosphate, sodium or potassium citrate and sodium or potassium carbonate. The sodium or potassium phosphate is preferably hydrogen- or dihydrogenphosphate, the sodium or potassium citrate is preferably hydrogen- or dihydrogencitrate, and the sodium or potassium carbonate is hydrogencarbonate. The amounts of the additives according to the present invention are not particularly limited, since they are determined depending on the amounts of lysozyme hydrochloride and dipotassium glycyrrhizinate. However, when lysozyme hydrochloride and dipotassium glycyrrhizinate are used in amounts of 0.1 wt. % and 0.25 wt. %, respectively, a preferred amount of sodium chloride is 0.5 to 1.5 wt. %, and that of sodium dihydrogenphosphate, sodium hydrogencarbonate, sodium hydrogenphosphate or potassium dihydrogenphosphate is 0.5 to 1.0 wt. %.

The solution of the present invention is prepared by adding water to a mixture of lysozyme hydrochloride, dipotassium glycyrrhizinate and the additive(s) of the present invention, then adding sodium hydroxide or the like thereto to adjust the pH of the solution to a given value and to obtain a solution, filtering the solution and, if necessary, sterilizing the filtrate. The solution of the present invention may further contain an antiseptic and other components which are not limited.

An effect of the present invention consists in that a solution containing lysozyme hydrochloride and dipotassium glycyrrhizinate which is clear at a pH in a physiological pH range of 5 to 9 can be provided. Therefore, the solution of the present invention is used mainly as eye drops, nasal drops, ear drops, and other external drugs to be applied to the oral cavity and throat. However, the form of the solution is not limited to them and the solution in other forms can also be used. For example, the technique of the preparation of the solution containing lysozyme hydrochloride and dipotassium glycyrrhizinate according to the present invention as described above can be employed in the preparation of cosmetics. Thus, the aqueous solution of the present invention can be used also in the cosmetic field.

[EXAMPLES]

The following examples will further illustrate the present invention and the effects of the present invention.

EXAMPLE 1

900 ml of distilled water was added to a mixture of 1 g of lysozyme hydrochloride, 2.5 g of dipotassium glycyrrhizinate and 8 g of sodium chloride to obtain a solution. The pH of the solution was adjusted to 7.0 with 0.1 N sodium hydroxide. Distilled water was added thereto to make up a total volume of 1,000 ml. After filtration under sterile conditions, 5 ml of the solution was poured into each of sealed containers under sterile conditions to prepare eye drops. The products were clear.

EXAMPLE 2

900 ml of distilled water was added to a mixture of 1 g of lysozyme hydrochloride, 2.5 g of dipotassium glycyrrhizinate, 10 g of sodium dihydrogenphosphate and 1 g of methylparaben to obtain a solution. The pH of the solution was adjusted to 7.4 with 0.1 N sodium hydroxide. Distilled water was added thereto to make up a total volume of 1,000 m(. After filtration under sterile conditions, 2 ml of the solution was poured into each of sealed containers under sterile conditions to prepare eye drops. The products were clear.

EXAMPLE 3

Distilled water was added to a mixture of 5 g of lysozyme hydrochloride, 2.5 g of dipotassium glycyrrhizinate and 20 g of potassium dihydrogenphosphate to obtain a solution. The pH of the solution was adjusted to 7.8 with 0.1 N sodium hydroxide. Distilled water was added thereto to make up a total volume of 1,000 ml. After filtration under sterile conditions, 5 ml of the solution was poured into each of sealed containers under sterile conditions to prepare eye drops. The products were clear.

EXAMPLE 4

Distilled water was added to a mixture of 1 g of lysozyme hydrochloride, 2.5 g of dipotassium glycyrrhizinate and 20 g of potassium chloride to obtain a solution. The pH of the solution was adjusted to 6.2 with 0.1 N sodium hydroxide. Distilled water was added thereto to make up a total volume of 1,000 ml. After filtration under sterile conditions, 10 m( of the solution was poured into each of sealed containers to prepare nasal drops. The products were clear.

EXAMPLE 5

Distilled water was added to a mixture of 1 g of lysozyme hydrochloride, 2.5 g of dipotassium glycyrrhizinate and 20 g of sodium hydrogenphosphate to obtain a solution. Distilled water was added thereto to make up a total volume of 1,000 ml. The pH of the solution was 8.0. After filtration under sterile conditions, 20 ml of the solution was poured into each of sealed containers under sterile conditions to prepare a drug to be applied to the throat. The products were clear.

EXAMPLE 6

Distilled water was added to a mixture of 5 g of lysozyme hydrochloride, 2.5 g of dipotassium glycyrrhizinate and 10 g of sodium hydrogencarbonate to obtain a solution. The pH of the solution was adjusted to 8.8 with 0.1 N sodium hydroxide. Distilled water was added thereto to make up a total volume of 1,000 ml. After filtration under sterile conditions, 5 ml of the solution was poured into each of sealed containers under sterile conditions to prepare ear drops. The products were clear.

EXAMPLE 7

Distilled water was added to a mixture of 1 g of lysozyme hydrochloride, 2.5 g of dipotassium glycyrrhizinate and 20 g of calcium chloride to obtain a solution. The pH of the solution was adjusted to 7.3 with 0.1 N sodium hydroxide. Distilled water was added thereto to make up a total volume of 1,000 ml. After filtration under sterile conditions, 5 ml of the solution was poured into each of sealed containers under sterile conditions to prepare eye drops. The products were clear.

EXAMPLE 8

Distilled water was added to a mixture of 0.1 g of lysozyme hydrochloride, 0.5 g of dipotassium glycyrrhizinate and 8 g of sodium chloride to obtain a solution. The pH of the solution was adjusted to 7.5 with 0.1 N sodium hydroxide. Then 40 g of glycerol, 20 g of sorbitol, 2 g of HCO-50 [polyoxyethylene hardened castor oil (50 mol of ethylene oxide added)] and a suitable amount of a flavor were added to the solution. The pH of the solution was adjusted to 7.0 with a solution of 1 g of methylparaben in 80 ml of ethanol. Distilled water was added thereto to make up a total volume of 1,000 ml. It was filtered to obtain a lotion. This lotion was clear.

EXAMPLE 9

Distilled water was added to a mixture of 1 g of lysozyme hydrochloride, 2.5 g of dipotassium glycyrrhizinate, 3 g of sodium hydrogenphosphate and 8 g of sodium chloride to obtain a solution. The pH of the solution was adjusted to 6.8 with 1 N sodium hydroxide.

Distilled water was added thereto to make up a total volume of 1,000 m(. This solution was clear.

EXAMPLE 10

Distilled water was added to a mixture of 1 g of lysozyme hydrochloride, 2.5 g of dipotassium glycyrrhizinate, 1 g of potassium chloride and 8 g of sodium chloride to obtain a solution. The pH of the solution was adjusted to 7.2 with 1 N sodium hydroxide. Distilled water was added thereto to make up a total volume of 1,000 m. This solution was clear.

EXAMPLE 11

Distilled water was added to a mixture of 1 g of lysozyme hydrochloride, 2.5 g of dipotassium glycyrrhizinate, 0.3 g of calcium chloride and 8.5 g of sodium chloride to obtain a solution. The pH of the solution was adjusted to 7.1 with 1 N sodium hydroxide. Distilled water was added thereto to make up a total volume 1,000 ml. This solution was clear.

EXAMPLE 12

Distilled water was added to a mixture of 1 g of lysozyme hydrochloride, 2.5 g of dipotassium glycyrrhizinate, 70 mg of potassium dihydrogenphosphate and 8.5 g of sodium chloride to obtain a solution. The pH of the solution was adjusted to 7.0 with 1 N sodium hydroxide. Distilled water was added thereto to make up a total volume 1,000 ml. This solution was clear.

EXAMPLE 13

Distilled water was added to a mixture of 1 g of lysozyme hydrochloride, 2.5 g of dipotassium glycyrrhizinate, 2 g of sodium hydrogencarbonate and 7 g of sodium chloride to obtain a solution. The pH of the solution was adjusted to 7.0 with 1 N sodium hydroxide. Distilled water was added thereto to make up a total volume of 1,000 ml. After filtration under sterile conditions, 5 ml of the solution was poured into each of sealed containers under sterile conditions to prepare dye drops. The products were clear.

EXAMPLE 14

Distilled water was added to a mixture of 1 g of lysozyme hydrochloride, 2.5 g of dipotassium glycyrrhizinate, 8 g of sodium chloride and 2 g of sodium dihydrogenphosphate to obtain a solution. The pH of the solution was adjusted to 7.3 with 1 N sodium hydroxide. Distilled water was added thereto to make up a total volume of 1,000 ml. This solution was clear.

EXAMPLE 15

Distilled water was added to a mixture of 1 g of lysozyme hydrochloride, 2.5 g of dipotassium glycyrrhizinate, 4 g of sodium dihydrogenphosphate and 6 g of sodium chloride to obtain a solution. The pH of the solution was adjusted to 6.8 with 1 N sodium hydroxide. Distilled water was added thereto to make up a total volume of 1,000 ml. This solution was clear.

EXAMPLE 16

Distilled water was added to a mixture of 1 g of lysozyme hydrochloride, 2.5 g of dipotassium glycyrrhizinate, 3 g of sodium citrate and 8 g of sodium chloride to obtain a solution. The pH of the solution was adjusted to 7.0 with 1 N sodium hydroxide. Distilled water was added thereto to make up a total volume of 1,000 ml. This solution was clear.

EXAMPLE 17

Distilled water was added to a mixture of 1 g of lysozyme hydrochloride, 2.5 g of dipotassium glycyrrhizinate, 6 g of sodium chloride and 8.3 g of sodium hydrogenphosphate to obtain a solution. The pH of the solution was adjusted to 7.0. Distilled water was added thereto to make up a total volume of 1,000 ml. This solution was clear.

EXAMPLE 18

Distilled water was added to a mixture of 1 g of lysozyme hydrochloride, 2.5 g of dipotassium glycyrrhizinate, 8 g of sodium chloride, 70 mg of sodium dihydrogenphosphate, 200 mg of potassium chloride and 200 mg of calcium chloride to obtain a solution. The pH of the solution was adjusted to 7.0 with 1 N sodium hydroxide. Distilled water was added thereto to make up a total volume of 1,000 ml. This solution was clear.

EXAMPLE 19

Distilled water was added to a mixture of 1 g of lysozyme hydrochloride, 2.5 g of dipotassium glycyrrhizinate, 7 g of sodium chloride, 1.0 g of potassium chloride and 1.0 g of sodium dihydrogenphosphate to obtain a solution. The pH of the solution was adjusted to 7.0. Distilled water was added thereto to make up a total volume of 1,000 ml. This solution was clear.

EXAMPLE 20

Distilled water was added to a mixture of 1 g of lysozyme hydrochloride, 2.5 g of dipotassium glycyrrhizinate, 1 g of potassium chloride, 5.5 g of sodium chloride, 10 g of sodium hydrogenphosphate and 2 g of sodium dihydrogenphosphate to obtain a solution. The pH of the solution was adjusted to 7.0. Distilled water was added thereto to make up a total volume of 1,000 ml. This solution was clear.

EXAMPLE 21

Distilled water was added to a mixture of 1 g of lysozyme hydrochloride, 2.5 g of dipotassium glycyrrhizinate, 8 g of sodium chloride, 70 mg of potassium dihydrogenphosphate and 0.2 g of potassium chloride to obtain a solution. The pH of the solution was adjusted to 7.0. Distilled water was added thereto to make up a total volume of 1,000 ml. This solution was clear.

EXAMPLE 22

Distilled water was added to a mixture of 1 g of lysozyme hydrochloride, 2.5 g of dipotassium glycyrrhizinate, 8 g of sodium chloride, 50 mg of potassium dihydrogenphosphate and 0.2 g of calcium chloride to obtain a solution. The pH of the solution was adjusted to 7.0. Distilled water was added thereto to make up a total volume of 1,000 ml. This solution was clear.

EXAMPLE 23

Distilled water was added to a mixture of 1 g of lysozyme hydrochloride, 2.5 g of dipotassium glycyrrhizinate, 8.5 g of sodium chloride, 2 g of potassium chloride and 0.2 g of calcium chloride to obtain a solution. The pH of the solution was adjusted to 7.0. Distilled water was added thereto to make up a total volume of 1,000 ml. This solution was clear.

EXAMPLE 24

Distilled water was added to a mixture of 1 g of lysozyme hydrochloride, 2.5 g of dipotassium glycyrrhizinate, 5.5 g of sodium chloride, 0.2 g of potassium chloride and 0.15 g of sodium hydrogenphosphate to obtain a solution. The pH of the solution was adjusted to 7.0. Distilled water was added thereto to make up a total volume of 1,000 ml. This solution was clear.

EXAMPLE 25

900 ml of distilled water was added to a mixture of 1 g of lysozyme hydrochloride, 2.5 g of dipotassium glycyrrhizinate and 15 g of sodium chloride to obtain a solution. The pH of the solution was adjusted to 5.0 with 0.1 N sodium hydroxide. Distilled water was added thereto to make up a total volume of 1,000 ml. This solution was clear.

EXAMPLE 26

900 ml of distilled water was added to a mixture of 1 g of lysozyme hydrochloride, 2.5 g of dipotassium glycyrrhizinate and 5 g of sodium hydrogencarbonate to obtain a solution. The pH of the solution was adjusted to 5.0 with 0.1 N hydrochloric acid. Distilled water was added thereto to make up a total volume of 1,000 ml. This solution was clear.

EXAMPLE 27

Distilled water was added to a mixture of 1 g of lysozyme hydrochloride, 2.5 g of dipotassium glycyrrhizinate, 0.3 g of magnesium chloride and 9 g of sodium chloride to obtain a solution. The pH of the solution was adjusted to 7.0 with 1 N sodium hydroxide. Distilled water was added thereto to make up a total volume of 1,000 ml. This solution was clear.

What is claimed is:

1. A clear aqueous solution which comprises a solution of lysozyme hydrochloride, dipotassium glycyrrhizinate, and at least one member selected from the group consisting of sodium chloride, potassium chloride, calcium chloride, magnesium chloride, sodium phosphate, potassium phosphate, sodium citrate, potassium citrate, sodium carbonate and potassium carbonate dissolved in water, said solution having a pH of 5 to 9.

2. A clear aqueous solution as claimed in claim 1, which comprises 0.1 to 0.5 percent by weight of lysozyme hydrochloride and 0.05 to 0.25 percent by weight of dipotassium glycyrrhizinate.

3. A clear aqueous solution as claimed in claim 1, in which said sodium phosphate is sodium hydrogen phosphate or sodium dihydrogen phosphate, said potassium phosphate is potassium hydrogen phosphate or potassium dihydrogen phosphate, said sodium citrate is sodium hydrogen citrate or sodium dihydrogen citrate, said potassium citrate is potassium hydrogen citrate or potassium dihydrogen citrate, said sodium carbonate is sodium hydrogen carbonate and said potassium carbonate is potassium hydrogen carbonate.

4. A clear aqueous solution as claimed in claim 1, which has a pH of 7.0 to 7.5.

5. A clear aqueous solution as claimed in claim 2, in which the weight ratio of lysozyme hydrochloride to dipotassium glycyrrhizinate is from 1/2.5 to 1/5.

6. A clear aqueous solution as claimed in claim 2, in which said solution has a pH of from 6.5 to 8.0.

7. A clear aqueous solution as claimed in claim 2, in which said solution has a pH of from 7.0 to 7.5.

8. A clear aqueous solution consisting essentially of from 0.1 to 0.5 percent by weight of lysozyme hydrochloride, from 0.05 to 0.25 percent by weight of dipotassium glycyrrhizinate, from 0.5 to 1.5 percent by weight of at least one member selected from the group consisting of sodium chloride, potassium chloride, calcium chloride, magnesium chloride, sodium hydrogen phosphate, sodium dihydrogen phosphate, potassium hydrogen phosphate, potassium dihydrogen phosphate, sodium hydrogen citrate, sodium dihydrogen citrate, potassium hydrogen citrate, potassium dihydrogen citrate, sodium hydrogen carbonate and potassium hydrogen carbonate, an amount of sodium hydroxide effective to make the pH of said solution in the range of 6.5 to 8.0, and the balance being essentially water.

* * * * *